US008888847B2

(12) United States Patent
Drew et al.

(10) Patent No.: US 8,888,847 B2
(45) Date of Patent: Nov. 18, 2014

(54) COVER HAVING SELF-ANCHORING PROTRUSIONS FOR USE WITH AN IMPLANTABLE MEDICAL DEVICE

(75) Inventors: Michael Hexiang Zhu Drew, Maple Grove, MN (US); Gary R. Noel, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 280 days.

(21) Appl. No.: 13/321,355

(22) PCT Filed: May 19, 2010

(86) PCT No.: PCT/US2010/035429
§ 371 (c)(1),
(2), (4) Date: Nov. 18, 2011

(87) PCT Pub. No.: WO2010/135440
PCT Pub. Date: Nov. 25, 2010

(65) Prior Publication Data
US 2012/0059467 A1 Mar. 8, 2012

Related U.S. Application Data

(60) Provisional application No. 61/180,833, filed on May 22, 2009.

(51) Int. Cl.
*A61F 2/02* (2006.01)
*A61N 1/375* (2006.01)

(52) U.S. Cl.
CPC .................................... *A61N 1/375* (2013.01)
USPC ...................................................... 623/11.11

(58) Field of Classification Search
USPC .......................................... 623/16.11, 23.73
See application file for complete search history.

(56) References Cited

U.S. PATENT DOCUMENTS

| 2,487,038 | A | 11/1949 | Jasper |
| 5,572,594 | A | 11/1996 | DeVoe et al. |
| 6,496,715 | B1 | 12/2002 | Lee et al. |
| 8,001,971 | B2 * | 8/2011 | Boucher et al. ............... 128/848 |
| 8,192,345 | B2 * | 6/2012 | Lamoureux et al. ............... 600/8 |
| 8,489,189 | B2 * | 7/2013 | Tronnes .......................... 607/36 |
| 2002/0072787 | A1 * | 6/2002 | Partridge et al. .............. 607/122 |
| 2002/0076075 | A1 | 6/2002 | Muller et al. |

(Continued)

FOREIGN PATENT DOCUMENTS

| EP | 0920239 | 6/1999 |
| WO | WO95/32673 | 12/1995 |

OTHER PUBLICATIONS

PCT/US10/035429: Search Report and Written Opinion dated Jul. 26, 2010.

*Primary Examiner* — Suzette J Gherbi

(57) ABSTRACT

A cover for receiving an implantable medical device includes self-anchoring protrusions that engage tissue of a pocket where the device is implanted to resist movement including rotation and flipping. The implantable medical device is placed into the cover prior to being placed into the pocket so that once in the pocket, the device may reduce rotating, flipping, or otherwise moving. The self-anchoring protrusions may include barbs of various shapes to frictionally engage the tissue of the pocket. The cover may include features such as a strap and elastic construction to assist in holding the implantable medical device within the cover. Apertures may be included to enable the device. The cover may include additional features like suture tabs to allow additional fixation via suturing the cover to the surrounding tissue.

26 Claims, 8 Drawing Sheets

(56) References Cited

U.S. PATENT DOCUMENTS

| | | |
|---|---|---|
| 2006/0095078 A1 | 5/2006 | Tronnes |
| 2007/0021642 A1* | 1/2007 | Lamoureux et al. .............. 600/4 |
| 2007/0123923 A1 | 5/2007 | Lindstrom et al. |
| 2008/0195188 A1 | 8/2008 | Libbus et al. |
| 2009/0082828 A1 | 3/2009 | Ostroff |
| 2009/0093765 A1 | 4/2009 | Glenn |
| 2012/0016176 A1* | 1/2012 | Lamoureux et al. .............. 600/8 |
| 2013/0211526 A1* | 8/2013 | Alheidt et al. ............. 623/17.16 |
| 2013/0231525 A1* | 9/2013 | Chu ............................... 600/37 |
| 2013/0253650 A1* | 9/2013 | Ashley et al. ............. 623/17.16 |

* cited by examiner

COVER HAVING SELF-ANCHORING PROTRUSIONS FOR USE WITH AN IMPLANTABLE MEDICAL DEVICE

RELATED CASES

This application is a U.S. National Stage filing under 35 U.S.C. 371 of copending PCT Application Serial No. PCT/US2010/035429, filed May 19, 2010, which claims priority to U.S. Provisional Patent Application No. 61/180,833, filed May 22, 2009, and both applications are hereby incorporated by reference as if re-written in its entirety.

TECHNICAL FIELD

Embodiments are related to covers for implantable medical devices. More particularly, embodiments are related to covers that include self-anchoring protrusions that resist movement of the implantable medical device.

BACKGROUND

Implantable medical devices (IMD) and associated implantable medical leads provide functions such as stimulation of muscle or neurological tissue and/or sensing of physiological occurrences within the body of a patient. Typically, the IMD is installed in a subcutaneous location that is accommodating and relatively accessible for implantation. For instance, to provide stimulation near the spine or pelvis, the IMD may be installed in a pocket located within the abdomen or upper buttocks region of the patient. For stimulation of the brain or heart, the IMD may be installed in a pocket located in the pectoral region. Stimulation leads are routed to the appropriate stimulation site and terminate at the pocket where they may be connected to the IMD.

After installation, movement of the IMD within the pocket, and rotational movement in particular, is a concern. An external housing of the IMD is typically a smooth metal such as titanium that does not resist movement relative to the tissue in the pocket. Such movement may result from the normal daily activities of the patient. Movement may also occur due to the patient manipulating the IMD position by grasping the IMD through the skin. The movement may cause various problems.

The implantable medical leads have electrical conductors within them. Typically, the lead is installed so that slack in the lead is removed. For instance, excess length of the lead may be wrapped about the IMD within the pocket to reduce the amount of slack. Excess movement of the IMD, and particularly rotation or flipping of the IMD, may stress the electrical conductors within the leads and cause breakage of the conductors. A surgical procedure to replace the broken lead may be necessary.

Another issue for IMDs that utilize unipolar stimulation is that the back side of a metal external housing of the IMD is coated with an insulator so that the front side of the metal can acts as one of the electrodes. Maintaining this housing electrode closest to the surface of the patient's body reduces the likelihood of uncomfortable sensations occurring within the tissue beneath the IMD. Should the IMD be flipped such that the uninsulated side of the metal can faces the tissue beneath the IMD, then the uncomfortable sensations become more likely.

Another issue occurs for IMDs that utilize a rechargeable battery and associated recharging circuitry. For these IMDs, the side of the IMD where a recharging coil is located is positioned closest to the surface of the patient's body so that energy transfer through an inductive coupling with an external coil can occur. Should the IMD be flipped such that the opposite side of the IMD becomes the closest to the surface of the patient's body, the inductive coupling is adversely affected and the IMD may not be properly recharged. If the IMD cannot be externally flipped back to the proper orientation, then a surgical procedure may be necessary to flip the IMD back to the original orientation so that recharging can commence.

SUMMARY

Embodiments address issues such as these and others by providing a cover for an implantable medical device. The cover includes self-anchoring protrusions that engage the tissue of the pocket to resist movement including rotation and flipping. The implantable medical device is placed into the cover prior to being placed into the pocket so that once in the pocket, the implantable medical device is less likely to rotate, flip, or otherwise move in a harmful manner.

Embodiments include a method of resisting movement of an implantable medical device having an external housing. The method involves providing a cover that includes self-anchoring protrusions and placing the implantable medical device within the cover. The method further involves placing the implantable medical device within the cover into a subcutaneous pocket of a patient.

Embodiments include a cover for an implantable medical device having an external housing. The cover includes a body comprising an inner region adapted to receive the implantable medical device. The cover also includes self-anchoring protrusions extending from the body.

Embodiments also include a kit. The kit includes an implantable medical device having an external housing and a cover having self-anchoring protrusions. The cover is sized to allow insertion of the implantable medical device into an inner region of the cover.

DETAILED DESCRIPTION

Figure 1:
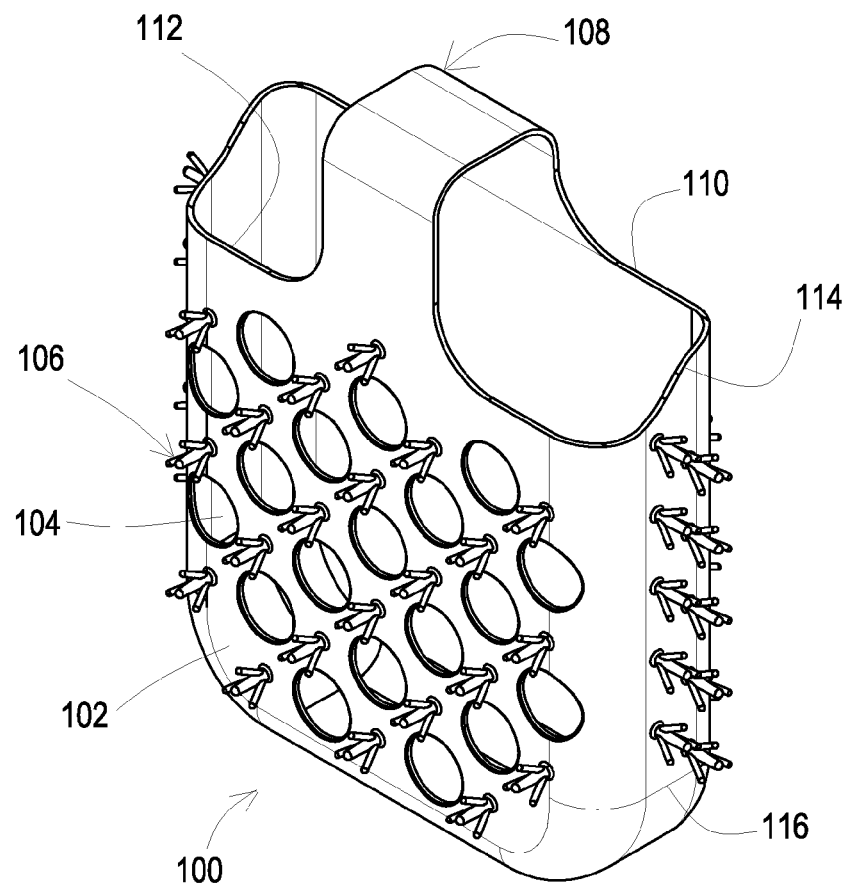
FIG. 1 is a perspective view of an illustrative cover embodiment for an implantable medical device.

Embodiments include covers for implantable medical devices (IMD) that provide self-anchoring protrusions. These self-anchoring protrusions engage with tissue of the pocket once the IMD has been placed into the cover and then implanted into the pocket. The self-anchoring protrusions thereby resist rotation, flipping, and other movements of the IMD.

FIGS. 1-5 and 8 show an illustrative embodiment of a cover 100. The cover 100 of this example forms a pouch having a front side 102, back side 122, left side 117, right side 116, and bottom side 119. The cover 100 of this example also includes a strap 108 that extends from a front top edge 112 to a back top edge 110. However, embodiments of the cover 100 may have various forms other than the pouch shown, such as a pouch with no strap 108, a sleeve with no bottom side 119 and no strap 108 or with the strap 108 and a second strap lapping over the bottom in place of the bottom side 119.

The cover 100 may be formed of various elastic biocompatible materials. For instance, liquid silicone rubber may be molded into the desired shape to form the cover 100. Examples of other such elastic biocompatible materials include enhanced tear resistance silicone (ETR). The elasticity allows the cover 100 to be stretched to accommodate insertion of an IMD 200 and to ultimately grip the IMD 200 to hold the IMD 200 in place within the cover 100. The elasticity may also allow self-anchoring protrusions 106 to be more compliant than a rigid material. This compliance allows the self-anchoring protrusions 106 to engage the tissue of the pocket to prevent troublesome rotation and other movement of the IMD 200 relative to the pocket yet not damage the tissue due to slight movement of the IMD 200 and cover 100 within the pocket.

Figure 2:
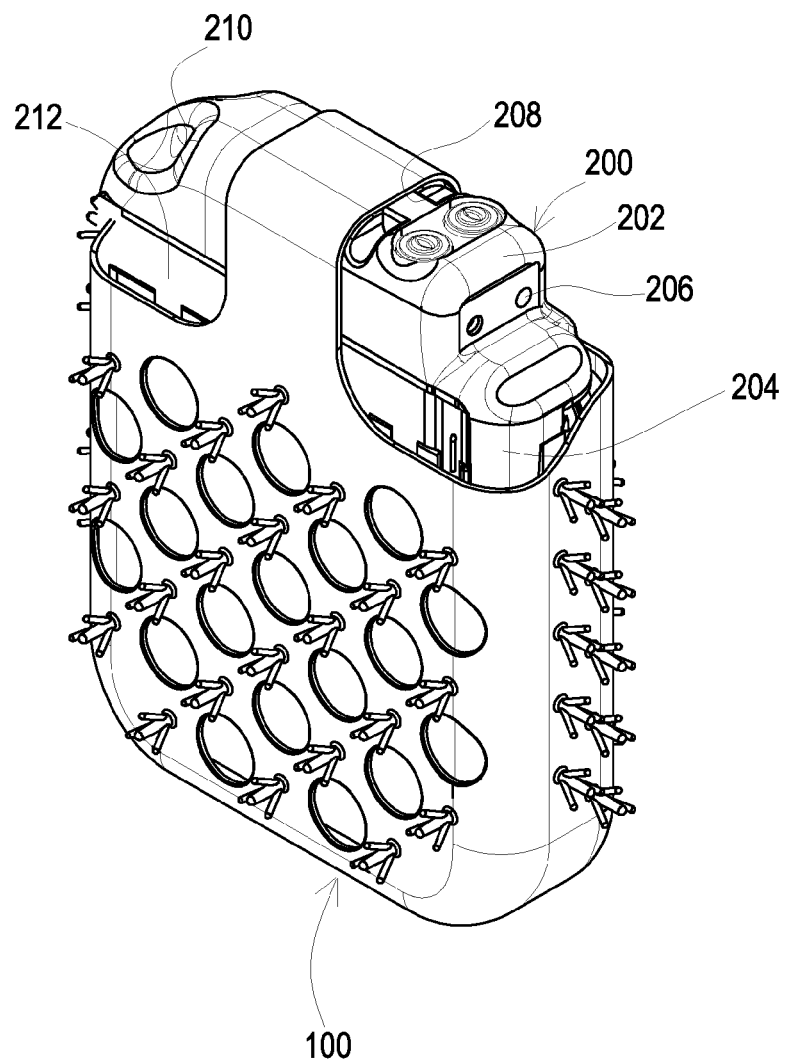
FIG. 2 is a perspective view of the illustrative cover with the implantable medical device positioned within an inner region of the cover.
Figure 3:
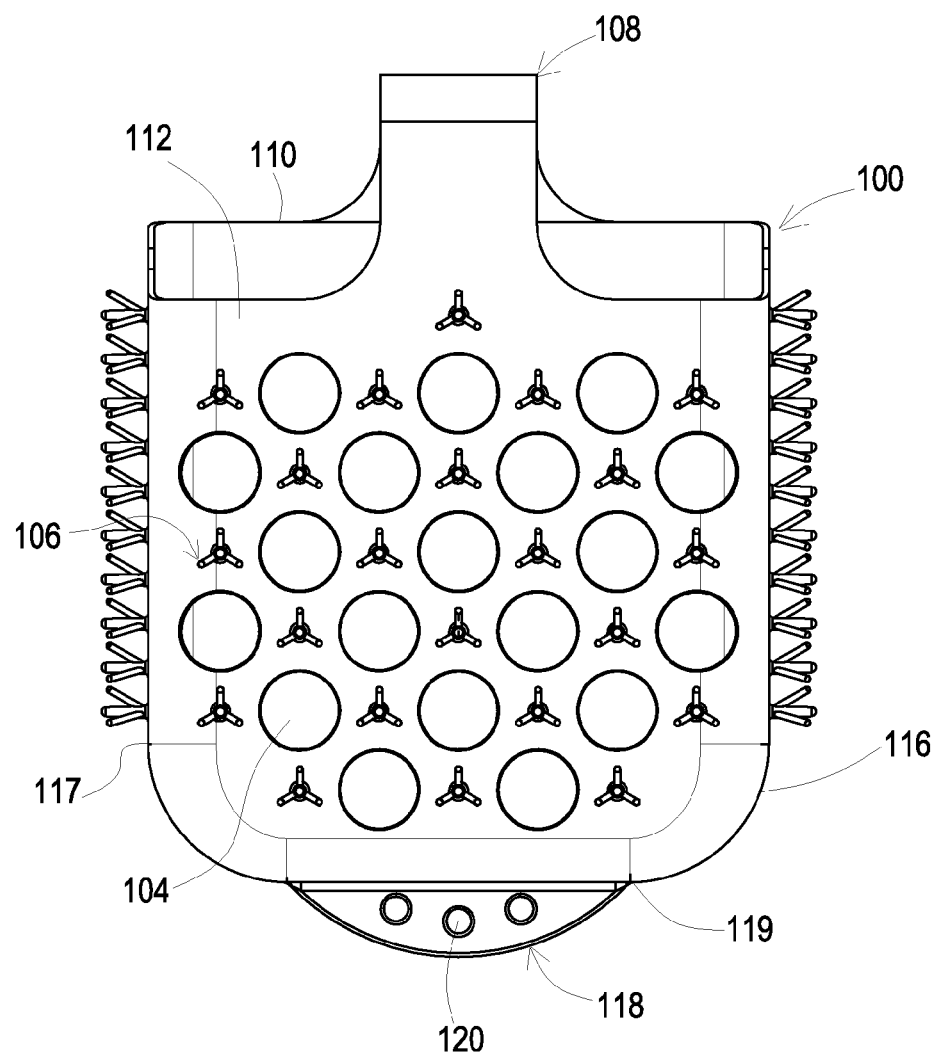
FIG. 3 is a front view of the illustrative cover.
Figure 4:
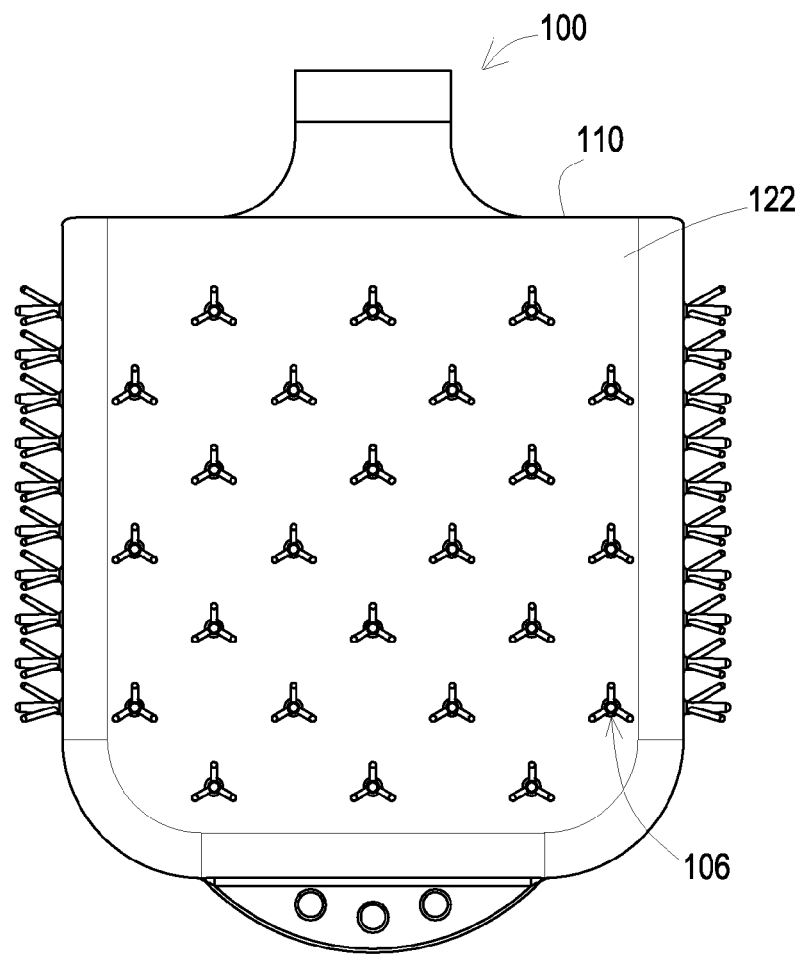
FIG. 4 is a rear view of the illustrative cover.
Figure 5:
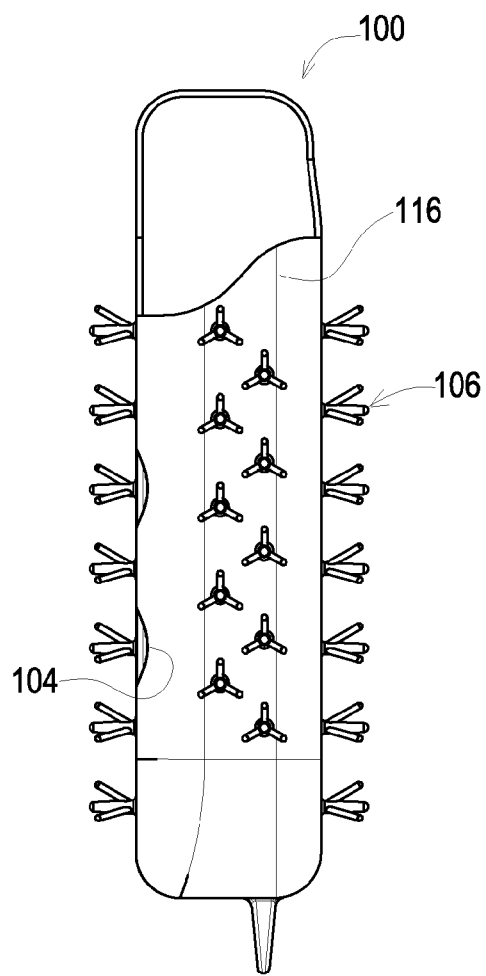
FIG. 5 is a side view of the illustrative cover.

As shown in FIG. 2, the IMD 200 may be placed within the inner region of the cover 100. For this particular example, the IMD 200 may be placed into the cover 100 by manually stretching the cover 100, and particularly the strap 108, so that the open top of the cover 100 is stretched to a sufficiently large size to allow the IMD 200 to be positioned into the cover 100. In this example, the metal external housing 204 of the IMD 200 extends down to the bottom side 119 of the cover 100 while a header 202 resides above the top edges 110, 112. The strap 108 laps over the header 202 in a slightly stretched state such that the strap 108 may apply force against the IMD 200 to aid in holding the IMD 200 within the cover 100. The lead openings 206 of the header 202 are exposed so that leads can be easily connected to the IMD 200 once the IMD 200 is placed within the cover 100.

In this particular example, the cover 100 includes apertures 104 on the front side 102 while the back side 122 remains solid. Additionally, in this example, the front top edge 112 is lower than the back top edge 110 and a side top edge 114 forms a taper. The apertures 104 and/or the lower front top edge 112 may be useful when the IMD 200 is employing unipolar stimulation which utilizes the metal outer surface of a can 204 of the IMD 200 as an electrode for the stimulation signal as it returns from an electrode of the lead back through the tissue to the IMD 200 to complete the electrical circuit. The metal outer surface of the can 204 being exposed through the apertures 104 and/or above the lower front top edge 112 provides the electrode contact for the unipolar stimulation.

The solid back side 122 provides adequate insulation of the metal outer surface of the can 204 on the back side of the IMD 200 such that the metal on the back side does not act as an electrode. This provides the added benefit that a non-conductive coating such as a parylene coating on the back side of the IMD 200 may be omitted thereby potentially reducing the costs associated with manufacturing the IMD 200. Furthermore, as the metal outer surface of the can 204 frictionally resides against the cover 100, the solid back side 122 provides a large surface area for gripping the IMD 200.

The apertures 104 and/or lower front top edge 112 may be included for additional purposes. For instance, where the IMD 200 uses a recharge coil, such as an external recharge coil 212, the apertures 104 and/or lower front top edge 112 may allow for ventilation of the recharge coil 212 where the recharge coil 212 is located in proximity to the apertures 104 once the IMD 200 is inserted into the cover 100. The apertures 104 and/or lower front top edge 112 may also allow for improved inductive coupling to an external coil during the recharging process as compared to a cover 100 not having apertures 104 or the lower front top edge 112.

Figure 6:
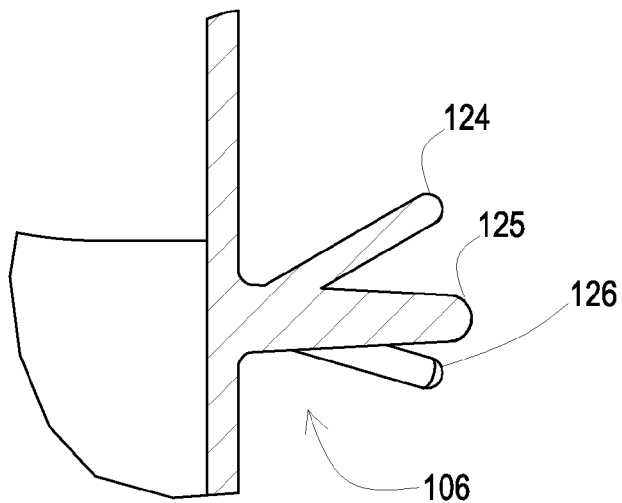
FIG. 6 is a side cross-sectional detail view of the self-anchoring protrusion of the illustrative cover.
Figure 7:
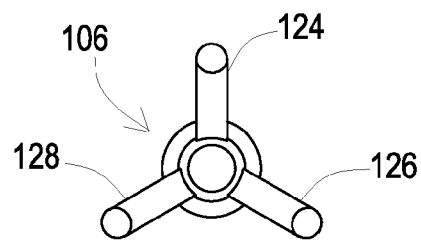
FIG. 7 is a top detail view of a self-anchoring protrusion of the illustrative cover.
Figure 8:
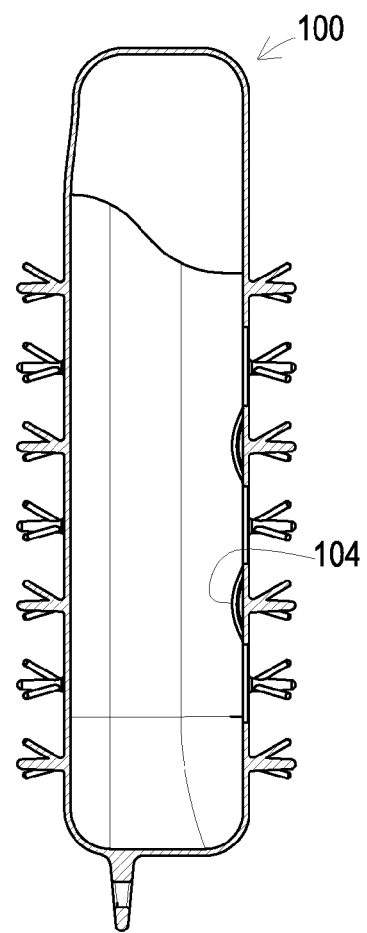
FIG. 8 is a cross-sectional side view of the illustrative cover.

The self-anchoring protrusions 106 may be of a variety of shapes. As shown in FIGS. 1-5 and 8, and in additional detail in FIGS. 6 and 7, an example of the self-anchoring protrusions 106 may be barbs having multiple prongs. Various other styles of self-anchoring protrusions may also be applicable, such as barbs having a different configuration of prongs, for instance longer or shorter prongs and/or prongs at different angles.

The self-anchoring protrusions 106 of the example shown are barbs having four prongs. A center prong 125 extends perpendicularly from the surface of the cover 100. Three peripheral prongs 124, 126, and 128 surround the center prong 125. The peripheral prongs 124, 126, and 128 are evenly spaced about the center prong 125 and extend from the center prong 125 so as to form an angle relative to the center prong 125 as well as relative to the surface of the cover 100. These prongs 124, 125, 126, and 128 engage the tissue so as to create a frictional relationship that resists movement. While a particular number and pattern of the self-anchoring protrusions 106 are shown, it will be appreciated that other numbers and patterns of self-anchoring protrusions 106 are also applicable.

The cover 100 may include additional features such as one or more suture tabs 118. The suture tab 118 includes holes 120 that allow a physician to suture the tab 118 to the tissue to further assist in fixing the position of the IMD 200 within the pocket. As shown, the suture tab 118 is positioned on the bottom side 119 and closer to the back side 122 than the front side 102. This may aid in the suturing where the physician sutures the tab 118 to the tissue that is immediately adjacent the back side 122. While a single suture tab 118 is shown on the bottom side 119, it will be appreciated that the suture tab 118 may be located on other sides of the cover 100 and/or that additional suture tabs may be located on the other sides.

The cover 100 may be sized such that it is slightly smaller in dimension when in the relaxed state than the IMD 200. As a result, where the cover 100 is made of an elastic material, the cover 100 may stretch to accommodate the IMD 200 within the inner region of the cover 100. The cover 100 grips the IMD 200 as the cover 100 attempts to shrink back to the dimensions of the relaxed state.

As one specific example which is provided for purposes of illustration, the illustrative cover 100 may have the following dimensions when in the relaxed state. These dimensions are complementary to an IMD 200 having a side to side width of 1.95 inches (4.95 cm), a top to bottom height of 2.60 inches (6.604 cm), and a front to back depth of 0.60 inches (1.524 cm).

The illustrative cover 100 may have a width from side 116 to side 117 of 1.992 inches (5.059 cm). The cover 100 may have a height from the bottom side 119 to the top of the strap 108 of 2.592 inches (7.498 cm). The height of the front top edge 112 from the bottom side 119 may be 1.870 inches (4.75 cm) while the height of the back top edge 110 from the bottom side 119 may be 2.120 inches (5.385 cm). The depth from the front side 102 to the back side 122 may be 0.593 inches (1.506 cm). The strap 108 may have a width of 0.500 inches (1.27 cm). The thickness of the silicone rubber may be 0.020 inches (0.050 cm).

The self-anchoring protrusions 106 of this illustrative example include various dimensions. The center prong 125 extends from the surface by 0.150 inches (0.381 cm) and has a diameter of 0.030 inches (0.076 cm). Each peripheral prong 124, 126, and 128 extends from the center prong 125 to form an angle of 60 degrees relative to the surface of the cover 100 and has a diameter of 0.020 inches (0.05 cm) with the tip being 0.130 inches (0.33 cm) away from the surface of the cover 100. The peripheral prongs are spaced about the center prong 125 by 120 degrees. The self-anchoring protrusions 106 are positioned in a staggered configuration where the center of the lowest protrusion on each side is 0.547 inches (1.389 cm) from the bottom edge with the center of the next lowest protrusion being 0.141 inches (0.358 cm) higher and 0.141 inches (0.358 cm) offset to the side. The center of the row of lowest protrusions 106 on the front and back sides 102, 122 is 0.293 inches (0.744 cm) from the bottom 119 with the center of the next lowest row of protrusions 106 being 0.255 inches (0.648 cm) higher and 0.255 inches (0.648 cm) offset to the side.

Other dimensions of this illustrative example may include an aperture diameter of 0.250 inches (0.635 cm). A suture tab height is 0.241 inches (0.612 cm) and a width is 0.075 inches (0.191 cm). The suture tab 118 is spaced from the back side 122 by 0.183 inches (0.465 cm).

Figure 9:
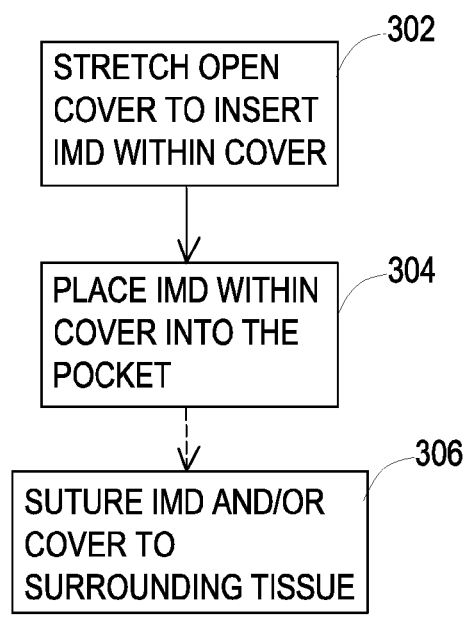
FIG. 9 is a procedural flow for utilizing the illustrative cover.

FIG. 9 shows a set of steps that may be performed to implement embodiments of the cover 100. The cover 100 and the IMD 200 may be provided as a kit to a physician. Initially, for embodiments where the kit includes the cover 100 and the IMD 200 as separate pieces, the cover 100 is stretched to a more open state so that the IMD 200 may be inserted into the inner region within the cover 100 at an insertion step 302. At this point, the pocket has been created either before or after the IMD 200 has been inserted into the cover 100. The IMD 200 which is within the cover 100 is then placed into position within the pocket at a placement step 304. The confinement of the pocket is such that the self-anchoring protrusions 106 engage the tissue of the walls of the pocket to provide frictional stabilization of the IMD 200. Furthermore, over time after the implantation there may be tissue in-growth around the engagement of the self-anchoring protrusions 106 to provide additional fixation.

While the self-anchoring protrusions 106 may provide resistance to movement, the physician may also decide to suture the IMD 200 to surrounding tissue of the pocket in a suturing step 306. The physician may suture the IMD 200 by suturing through the suture openings 210 and/or 208 of the IMD 200 that are exposed on each side of the strap 108. The physician may additionally or alternatively choose to suture through one or more of the holes 120 of the suture tab 118 on the cover 100.

While embodiments have been particularly shown and described, it will be understood by those skilled in the art that various other changes in the form and details may be made therein without departing from the spirit and scope of the invention.

What is claimed is:

1. A method of reducing occurrences of flipping of an implantable medical device having an external housing, comprising:
    providing a cover that includes self-anchoring protrusions;
    placing the implantable medical device within the cover; and
    placing the implantable medical device that is within the cover into a subcutaneous pocket of a patient,
    wherein the self-anchoring protrusions comprise barbs and wherein the barbs comprise a central prong extending perpendicularly from a surface of the cover and three peripheral prongs extending at an angle from the central prong.

2. The method of claim 1, wherein the cover is a pouch having at least a front side, back side, left side, right side, and bottom side.

3. The method of claim 1, wherein the cover comprises an elastic biocompatible material.

4. The method of claim 3, wherein the elastic biocompatible material is silicone rubber.

5. The method of claim 1, wherein the cover comprises a suture tab.

6. The method of claim 5, further comprising suturing the cover to tissue via a hole of the suture tab.

7. The method of claim 1, wherein the cover comprises apertures on a front side with a solid back side such that a metal outer surface of the implantable medical device is exposed through the apertures on the front side and is insulated by the cover on the back side.

8. The method of claim 1, wherein the cover comprises a front side with a lower top edge than a top edge of a back side of the cover.

9. The method of claim 1, wherein the cover comprises a strap extending from a front top edge to a back top edge of the cover, the strap exerting force upon the implantable medical device when the implantable medical device is placed within the cover and wherein the strap borders at least one opening from the front top edge to the back top edge.

10. The method of claim 9, further comprising suturing the implantable medical device to tissue via a suture hole of the implantable medical device that is exposed via the opening from the front top edge to the back top edge of the cover.

11. The method of claim 1, further comprising providing the implantable medical device with a metal outer surface that frictionally resides against the cover.

12. The method of claim 1, further comprising providing the implantable medical device with a recharging coil, the recharging coil being in proximity to the apertures when the implantable medical device is placed within the cover.

13. A cover for an implantable medical device having an external housing, comprising:
    a body comprising an inner region adapted to receive the implantable medical device, the body having at least a front side, a back side, a left side, a right side, and a bottom side, the front side having a top edge, the back side having a top edge, the left side having a top edge, and the right side having a top edge, where each of the top edges together forms an open top that exposes the inner region; and
    self-anchoring protrusions extending from the body.

14. The cover of claim 13, wherein the body is sized to grip the external housing of the implantable medical device once the implantable medical device is received into the inner region.

15. The cover of claim 13, wherein the body comprises an elastic biocompatible material.

16. The cover of claim 15, wherein the elastic biocompatible material is silicone rubber.

17. The cover of claim 13, wherein the self-anchoring protrusions comprise barbs.

18. A cover for an implantable medical device having an external housing, comprising:
    a body comprising an inner region adapted to receive the implantable medical device and
    self-anchoring protrusions extending from the body,
    wherein the self-anchoring protrusions comprise barbs, wherein the barbs comprise a central prong extending perpendicularly from a surface of the body and three peripheral prongs extending at an angle from the central prong.

19. A cover for an implantable medical device having an external housing, comprising:
    a body comprising an inner region adapted to receive the implantable medical device;
    self-anchoring protrusions extending from the body; and
    a suture tab extending from the body.

20. A cover for an implantable medical device having an external housing, comprising:
    a body comprising an inner region adapted to receive the implantable medical device;
    self-anchoring protrusions extending from the body; and
    apertures on a front side of the body with a solid back side of the body.

21. A cover for an implantable medical device having an external housing, comprising:
    a body comprising an inner region adapted to receive the implantable medical device;
    self-anchoring protrusions extending from the body; and
    wherein a front side of the body has a lower top edge than a top edge of a back side of the body.

22. A cover for an implantable medical device having an external housing, comprising:
    a body comprising an inner region adapted to receive the implantable medical device;
    self-anchoring protrusions extending from the body; and
    a strap extending from a front top edge of the body to a back top edge of the body, the strap bordering at least one opening from the front top edge to the back top edge.

23. A method of reducing occurrences of flipping of an implantable medical device having an external housing, comprising:
    providing a cover that includes self-anchoring protrusions;
    placing the implantable medical device within the cover; and
    placing the implantable medical device that is within the cover into a subcutaneous pocket of a patient,
    wherein the cover comprises a suture tab.

24. A method of reducing occurrences of flipping of an implantable medical device having an external housing, comprising:
    providing a cover that includes self-anchoring protrusions;
    placing the implantable medical device within the cover; and
    placing the implantable medical device that is within the cover into a subcutaneous pocket of a patient,
    wherein the cover comprises apertures on a front side with a solid back side such that a metal outer surface of the implantable medical device is exposed through the apertures on the front side and is insulated by the cover on the back side.

25. A method of reducing occurrences of flipping of an implantable medical device having an external housing, comprising:
    providing a cover that includes self-anchoring protrusions;
    placing the implantable medical device within the cover; and
    placing the implantable medical device that is within the cover into a subcutaneous pocket of a patient,
    wherein the cover comprises a front side with a lower top edge than a top edge of a back side of the cover.

26. A method of reducing occurrences of flipping of an implantable medical device having an external housing, comprising:
    providing a cover that includes self-anchoring protrusions;
    placing the implantable medical device within the cover; and
    placing the implantable medical device that is within the cover into a subcutaneous pocket of a patient,
    wherein the cover comprises a strap extending from a front top edge to a back top edge of the cover, the strap exerting force upon the implantable medical device when the implantable medical device is placed within the cover and wherein the strap borders at least one opening from the front top edge to the back top edge.

* * * * *